United States Patent
Carey et al.

(10) Patent No.: US 9,486,648 B2
(45) Date of Patent: Nov. 8, 2016

(54) POSITIONING SYSTEM FOR RADIOTHERAPY TREATMENT

(71) Applicant: Elekta AB, Stockholm (SE)

(72) Inventors: Peter Carey, Sunnyvale, CA (US); Paul Barry, Quebec (CA)

(73) Assignee: ELEKTA AB, Stockholm (SE)

( * ) Notice: Subject to any disclaimer, the term of this patent is extended or adjusted under 35 U.S.C. 154(b) by 193 days.

(21) Appl. No.: 14/466,558

(22) Filed: Aug. 22, 2014

(65) Prior Publication Data

US 2015/0057485 A1 Feb. 26, 2015

(30) Foreign Application Priority Data

Aug. 23, 2013 (GB) .................................. 1315075.0

(51) Int. Cl.
*A61N 5/10* (2006.01)

(52) U.S. Cl.
CPC ............ *A61N 5/1049* (2013.01); *A61B 90/39* (2016.02); *A61B 90/96* (2016.02); *A61B 2090/3937* (2016.02); *A61N 2005/1059* (2013.01)

(58) Field of Classification Search
CPC ........ A61B 6/08; A61B 6/587; A61B 6/547; A61B 6/0492; A61B 6/06; A61N 5/1049; A61N 2005/105; A61N 2005/1056
See application file for complete search history.

(56) References Cited

U.S. PATENT DOCUMENTS

| 5,537,453 A * | 7/1996 | Williams .................. A61B 6/08 378/205 |
| 2005/0049483 A1 | 3/2005 | Vorbuchner |
| 2008/0064953 A1 * | 3/2008 | Falco ....................... A61B 8/08 600/427 |

FOREIGN PATENT DOCUMENTS

WO WO 2005/044378 A1 5/2005

OTHER PUBLICATIONS

GB Search Report, issued in corresponding Application No. GB1315075.0, dated Feb. 13, 2014, one (1) page.

* cited by examiner

*Primary Examiner* — Hoon Song
(74) *Attorney, Agent, or Firm* — Finnegan, Henderson, Farabow, Garrett & Dunner, LLP

(57) ABSTRACT

An apparatus for placement of an optical marker for radiotherapy onto a surface, wherein the optical marker has a reflective element positioned on a body having an outline and shaped and configured such that the reflective element is in a predetermined position relative to the outline of the body, the apparatus comprising a sheet of material having a hole therethrough which is shaped and configured to conform to the outline of the body and which has an upper surface with markings thereon configured for aligning with an image projected onto the surface on which the optical marker is to be placed.

14 Claims, 2 Drawing Sheets

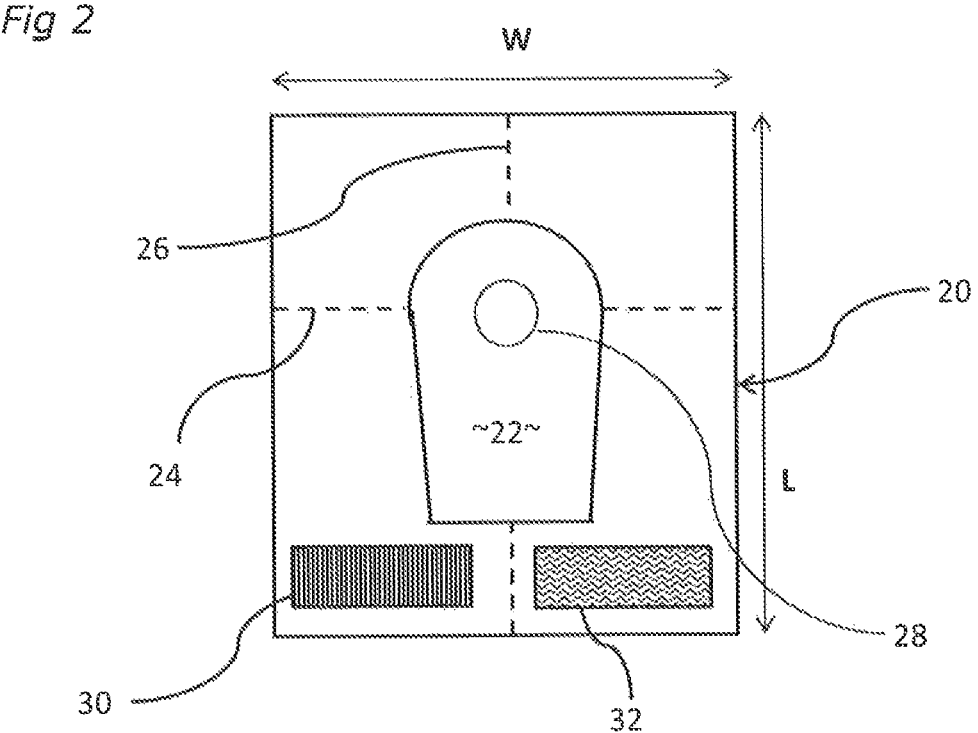

POSITIONING SYSTEM FOR RADIOTHERAPY TREATMENT

CROSS REFERENCE TO RELATED APPLICATION

The present application claims the benefits of priority to GB 1315075.0, filed Aug. 23, 2013. The entire content of the above referenced application is incorporated herein by reference.

FIELD OF THE INVENTION

The invention relates to apparatus for the positioning and/or identification of equipment and/or a patient for the purpose of radiotherapy treatment or diagnosis.

BACKGROUND ART

Positioning systems are used for the accurate and reproducible positioning of patients and equipment for radiation therapy, diagnostic imaging, surgery and other medical procedures (hereinafter all these are referred to collectively as "radiotherapy treatments"). For modern radiotherapy treatments, precise positioning is imperative; accurate positioning is not only necessary for the patient, but also for accessories, such as supports for the patient or parts of the patient's body (e.g. body bags or cushions, headsteps, neck supports, kneesteps, etc.), or other items of equipment which are employed during radiotherapy. Positioning is normally relative to the room or facility in which the radiotherapy is to take place, in particular relative to the treatment apparatus itself (the apparatus which generates the radiation for the radiotherapeutic treatment). This apparatus is usually large and heavy, so the patient and/or accessories are usually placed on a support, or table, which is moveable and has at least three translational degrees of freedom and often additional rotational degrees of freedom. In many cases, once the patient, and any accessories, are correctly positioned relative to the radiation apparatus (for example by moving the table on which the patient is supported), the radiotherapy apparatus moves relative to the patient during the radiotherapy treatment so as to direct a beam of radiation towards the patient from a number of different directions, to irradiate a desired region sufficiently whilst reducing the radiation dose applied to healthy tissue lying around the desired region; this is usually done by mounting the radiation source on a gantry which is free to rotate in an arc around the patient, thus allowing the radiation beam to be precisely directed and the radiation dose to be accurately controlled. These movements are typically controlled by patient and gantry control computers, and a radiation control computer controls the radiation generation, all according to a treatment planning computer; these may physically be one or more computers, or they may be discrete functional elements of a single computer.

Radiotherapy treatments are often set out in complex treatment plans, requiring the patient to undergo repeated radiotherapy treatments at intervals which can span a considerable time. This necessitates ensuring, every time that the patient attends for radiotherapy treatment, not only that the patient and any accessories or other equipment are accurately positioned, but also that the patient and the accessories or other equipment are correctly identified and match the treatment plan. The treatment plan is usually defined by a consultant physician, and translated into a plan which is capable of being carried out by the apparatus by a radiologist, with this plan being held in the treatment planning computer. When a patient attends for radiotherapy treatment, an operator calls up the appropriate treatment plan for that patient, ensures that the patient and all the necessary accessories/other items of equipment are present, match the treatment plan and are correctly positioned. This process of preparing the patient for the radiotherapy treatment (or "set up") is complicated and takes time to carry out correctly, but is absolutely necessary to ensure patient safety and that the radiotherapy treatment is properly and effectively carried out. Reducing this set up time will improve the efficacy and safety of treatment and increase patient throughput, and many workflow management systems have been suggested to achieve this, often integrated with the treatment planning computer.

Systems employing radiofrequency identification (RFID) tags have been used for identification of the patient and any accessories or other equipments, but these are not yet sufficiently accurate to be used as the sole means of patient positioning (RFID tags are currently accurate to about 1 cm, whereas the radiotherapy treatment requires greater precision, of 1 mm or less). Light or laser projectors are used in nearly all radiotherapy treatment facilities to assist in positioning for radiotherapy treatment; beams of light are projected to form crosses on the accessory/skin of the patient. The projections are aligned with a predetermined area on the accessory/patient, which may be denoted by marks or stickers applied to the accessory/patient's skin. Photogrammetry-based systems have been used for positioning the patient, in which optically reflective markers affixed to the patient are tracked by infrared cameras, so that the accessory/patient can be accurately positioned initially (assuming that the marker has been accurately positioned on the patient's skin), and such systems are able to monitor any movement of the patient with sufficient accuracy during treatment, and sound an alert or interrupt the treatment in the event the movement exceeds a threshold which would seriously affect the radiotherapy treatment or risk harm to the patient.

SUMMARY OF THE INVENTION

The present invention provides an apparatus for placement onto a surface of an optical marker for radiotherapy, wherein the optical marker has a reflective element positioned on a substrate having an outline and shaped and configured such that the reflective element is in a predetermined position relative to the outline of the substrate, the apparatus comprising a sheet of material having a hole in and passing through it and which is shaped and configured to conform to the outline of the substrate and having an upper surface with markings thereon configured for aligning with an image projected onto the surface on which the optical marker is to be placed.

Such an arrangement allows accurate and, significantly, reproducibly accurate placement of the optical marker on a patient or any accessory or other equipment. This allows the accurate and reproducible positioning of a patient or any accessory or other equipment relative to the radiotherapy apparatus on initial set up, and also permits the accurate tracking of movement during the radiotherapy treatment by photogrammetry. In addition, the sheet can be provided with identification markings similar to those on the optical markers. This facilitates identification of the correct optical marker for a particular patient, or the appropriate accessory. Accordingly the present invention combines aspects of conventional systems for positioning or identification for radiotherapy treatment, but improves both positioning as well as identification, but reduces the speed of set up, provides improved reproducibility and can be utilised for both a patient and items of equipment or accessories.

The sheet may be thin, and it may be flexible, for applying to a curved surface, such as a patient's body, or it may be rigid which may be more appropriate in the case of an item of equipment/accessory; it may have an adhesive backing (like the optical marker), so that when it is positioned accurately relative to a patient or other item it can be relied on to stay in position for as long as required. The sheet may be provided with identification markings to enable the sheet to be accurately matched with the identification markings on the optical marker (the markings on the two may be similar); these markings may include barcodes or other markings suitable for being read photogrammetrically, and/or words or symbols easily read by a human operator. In this way, sheets can be matched to the respective optical markers and to the appropriate surfaces to which they are to be affixed/positioned, making set up quicker and easier.

Additionally or alternatively the markings may include lines, such as two lines; these lines, which may be printed on or formed as grooves in the sheets, may form a cross. This enables the sheets to be easily aligned with the laser (or light) projection on the surface, to act as an indication as to where the optical marker is to be positioned. The crossing of the lines may be within the outline of the upper surface of the sheet, and may be within the hole in the sheet. This facilitates accurate manual positioning of the sheet relative to the surface against which the optical marker is to be positioned, with an operator having to position the hole over the intersecting lines of the projected cross, thus coarsely positioning the sheet, and then accurately positioning it by moving the sheet so that the lines marked on it coincide with the projected lines.

As is known, the reflective element may be an optical reflector, such as an infrared reflector, and it may be a spherical reflector.

The invention also provides a method of placement on a surface of an optical marker for radiotherapy comprising the steps of: a) projecting an image onto the said surface to identify a position on said surface where the optical marker is to be placed; b) aligning a sheet with the projected image so that a hole in the sheet is located in a predetermined position and/or orientation relative to said position, and c) aligning the optical marker with the hole in the sheet.

Afterwards, the optical marker can be fixed to the said surface and the sheet then removed. Before step b), the surface relative to which the optical marker is to be positioned can be placed onto a movable support surface, the optical marker placed on the said surface at the desired placement location, and the support surface moved relative to the projected image so that the projected image coincides with a reflective portion of the optical marker. The amount of movement required for this can be measured and recorded (for example by the treatment planning computer), to allow the accurate positioning to be reproduced at a later time. The surface to which the optical marker is to be placed can be a surface of an apparatus for use in the radiotherapy treatment, or it can be a surface of a patient to be subjected to the radiotherapy treatment.

BRIEF DESCRIPTION OF THE DRAWINGS

The invention will now be described by way of example and with reference to the accompanying figures, in which:

FIG. 2 is a schematic plan view of an embodiment of the present invention.

DETAILED DESCRIPTION OF THE EMBODIMENTS

Figure 1:
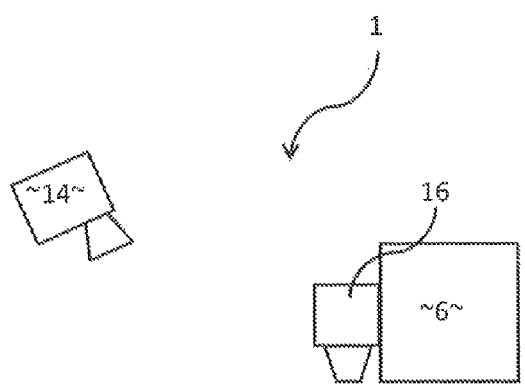
FIG. 1 is a schematic side view of a radiotherapy treatment facility in which the present invention may be applied.
Figure 1:
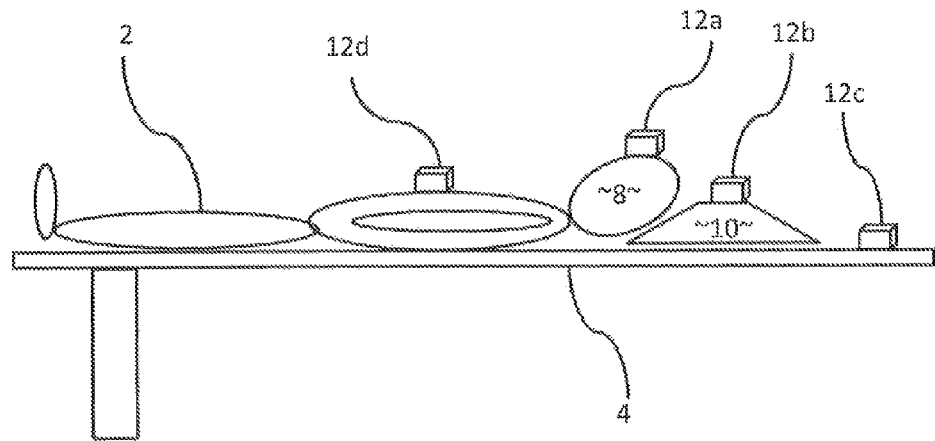

FIG. 1 shows a radiotherapy treatment system 1 in which a patient 2 is lying on a patient support 4 for radiotherapy treatment generated by a radiation source 6 such as a linear accelerator. The patient support 4 and/or the radiation source 6 are movable so that radiation can be directed at the patient 2 from any desired direction; in this example, the radiation treatment is to be applied to the patient's head 8. The patient's head 8 is supported on a headstep 10. In order for the radiotherapy treatment to be carried out properly as planned, it is important that the patient's head 8 is accurately positioned relative to the patient support 4, which is dependent also on the position of the headstep 10 relative to both the patient support 4 and the patient 2 and/or the patient's head 8. This positioning is monitored photogrammetrically by way of optical markers 12a, 12b and 12c which are fixed to the patient's head 8, the headstep 8 and the patient support 4 respectively; a further optical marker 12d is shown positioned on the body of the patient 2. The position and, optionally, orientation of these optical markers is monitored by optical tracking system 14, such as an infrared camera, which has a positional accuracy of at least 4 mm and preferably better. The radiation source 6, optical tracking system 14 and the systems (not shown) for moving the radiation source 8 and the patient support 4 are operatively connected to, and controlled by, a treatment planning computer (not shown) as described above, all forming part of the system 1.

The optical tracker 14 is not only capable of detecting the position of the optical markers 12a-d, but also of reading identification markings on the optical markers (such as a barcode). Thus the system 1, via the optical tracker 14, can identify that the appropriate headstep 10 is in use with this patient 2, that the patient 2 and headstep 10 correspond to the treatment plan held in the treatment planning computer for this particular radiotherapy treatment procedure, and also monitor the position and/or alignment of the patient 2, the patient's head 8 and the headstep 10 in the initial set up phase and also during the treatment, so as to ensure that the radiation treatment is correctly applied. These identification and positioning steps are suitably carried out in an automated fashion, as is known in the art, with audible and/or visual alerts being provided to the operator of the system 1.

Accurate positioning of the patient 2 and the headstep 10 relative to the patient support 4 requires that the optical trackers 12a, 12b, 12c, 12d be accurately positioned relative to the surfaces to which they are fixed. This can be done by eye, aided by projector 16 (which is shown aligned with the beam of radiation emitted by the source 6, but which does not have to be so aligned) which projects an image onto the surface to which the optical marker is to be fixed, but although this might provide adequate accuracy for a single radiotherapy treatment it is not accurately reproducible from one treatment to the next, so that during a course of radiotherapy treatments there is a risk that successive treatments may not be aligned so that the overall treatment plan is not carried out exactly as planned.

The positioning of the optical markers 12a-d is carried out using a sheet, or stencil, 20, shown in FIG. 3. The sheet 20 has a hole 22 positioned substantially centrally, the outline of the hole being the same shape but slightly larger than the outline of the optical marker (not shown). Two lines 24, 25 are drawn on the surface of the sheet, so as to intersect at the centre of the hole 22, coincident with the centre of the reflective element of the optical marker when placed in the hole 22 (the position of the reflective element, if the optical marker were positioned within the hole 22, being indicated by the circular outline 28, whose centre is at the intersection of lines 24, 26).

The sheet 20 is shown as rectangular (although it could be of any shape); for a typical optical marker, which is to be mounted to a flat surface, the length L of the sheet 3 would be about 8 cm and the width about 7 cm, and the border of the sheet 20 extends beyond the longest point of the optical marker by about 2 cm. In some situations an inclined optical marker has to be applied (where, for example, the optical marker has to be applied to a surface of limited area, and/or which in use is applied to a surface which is inclined at an angle away from the optical tracker 14 (FIG. 1); such inclined optical markers are usually smaller, as is the sheet 8 for use in positioning such a marker, being about 4.7 cm in length and about 4.5 cm in width, but the outline of the inclined optical marker, and the hole in the sheet for use with such a marker, is broadly similar to that shown in FIG. 2, with the border of the sheet extending beyond the longest point of the optical marker by about 0.5 cm.

The sheet 20 is also provided with markings, one of which 30 is adapted to be readable by the optical tracking system, such as a barcode, and the other of which 32 is readable by an operator. Markings 30, 32 are for identification purposes, and identify the item to which the optical marker is to be applied, and/or the patient. Conveniently, these markings may be similar to markings applied to the optical marker, so that the appropriate sheet 20 can be matched to the relevant optical marker and to the intended surface (i.e. the patient, or an accessory or other item of equipment) to which the optical marker is to be fixed; the two different markings mean that this matching can be carried out by both an operator and the optical tracker system/treatment planning computer.

The purpose of the lines 24, 26 is to allow the sheet 20 to be accurately positioned and orientated with the aid of a laser or other projector system. The projector system (not shown) projects beams of light along the isocentric planes of the radiation beam, creating a cross on the surface to which the optical tracker is to be mounted, and the operator places the sheet 20 against the surface so that the projected cross appears in the centre of the hole, at the intersection of the lines 24, 26. Then the operator adjusts the position and orientation of the sheet 20 so that the intersection of the lines 24, 26 is coincident with the centre of the projected cross image, and so that the lines 24, 26 are aligned with the lines of the projected cross. Then the sheet 20 can be temporarily fixed in position (by means of a self-adhesive rear surface, for example). An optical marker is then checked against the markings 30, 32 to ensure it is the correct one, and fixed to the surface through the hole in the sheet 20 (with a suitable adhesive, for example). Then the sheet 20 can be peeled away, leaving the correct optical marker accurately fixed in position on the underlying surface ready for the radiotherapy treatment to commence.

The process for locating an optical marker on an accessory, or other item of equipment is set out below (the process for locating a marker on a patient is similar). The optical tracker/treatment planning system determines if the optical marker is in an acceptable position by comparing the current position with the position defined during the initial setup.

1 Place the accessory on the patient support referenced to a fixed point of the patient support.

2 Place the optical marker on the accessory at the desired location. Do not yet use the adhesive backing to secure the optical marker to the accessory.

3 Move the patient support so that the optical marker is centred in the projected laser lines.

4 Select the appropriate sheet/stencil (flat or inclined) for the optical marker.

5 Remove the optical marker and thoroughly clean the surface area under the optical marker.

6 Align the sheet/stencil with the projected laser lines and attach it to the accessory.

7 Remove the backing from the self-adhesive surface of the optical marker and place it in the hole in the sheet.

8 Firmly press the optical marker onto the accessory.

9 Record the following information:

Position of the patient support (X, Y, Z, iso rotation).

reference position in relation to which the accessory is mounted

Barcode of the optical marker

Configuration of the accessory (for example, if an arm or other part of the accessory must be extended or adjusted for positioning)

10 Carefully remove the stencil, leaving the optical marker in place.

For identical, non-patient-specific accessories (accessories that are not specially configured for a certain patient), the optical markers must be attached in exactly same location for each radiotherapy treatment. For patient-specific accessories (accessories that have been set up for a certain patient for the duration of the treatment), the optical markers do not have to be attached in exactly the same location and the same applies where optical trackers are attached to the patient. However, for optical markers which are applied patient-specifically, careful positioning of the optical markers so as to be close to a previously-used location reduces the corrections the treatment planning computer must make before commencing treatment.

When setting up identical non-patient-specific accessories for a subsequent treatment, the following process applies:

1 On the treatment planning computer, select the patient and treatment plan set up for the accessory.

2 Place the accessory in the previously documented position.

3 Move the patient support to the previously documented position. The required location of the optical marker should now be in the lasers.

4 Align the appropriate sheet/stencil (flat or inclined) to the projected laser lines and attach it to the accessory.

5 Remove the backing from the self-adhesive surface of the optical marker and place the optical marker in the hole in the sheet.

6 Firmly press the optical marker onto the accessory.

7 Carefully remove the sheet/stencil, leaving the optical marker in place.

It will of course be understood that many variations may be made to the above-described embodiment without departing from the scope of the present invention. For example, the sheet 20 may be rigid, or it may be flexible (so as to conform to a curved surface or to ease application/removal), it may be any suitable shape other than rectangular, and it may be of any suitable size and/or thickness. The lines 24, 26 on the sheet may be drawn or printed, or they may be grooves formed in the surface of the sheet 20. The markings 30, 32 may be located anywhere which is convenient on the sheet, provided they can be easily read by the operator and/or the optical tracker. The system described may be utilised in combination with conventional identification systems, such as RFID tags, for added safety and reliability. The invention has been described with reference to lasers which project lines which intersect to form an image of a cross, however the projected image could be any other shape, such as a square, triangle, circle or the like, and in such cases the markings on the sheet would be altered to match; the lines could be continuous or interrupted, and they can form an orthogonal cross or intersect at any angle other than 90 degrees.

Furthermore, where different variations or alternative arrangements are described above, it should be understood that embodiments of the invention may incorporate such variations and/or alternatives in any suitable combination.

The invention claimed is:

1. An apparatus for placement onto a surface of an associated optical marker for radiotherapy, wherein the optical marker has a reflective element positioned on a substrate having an outline and shaped and configured such that the reflective element is in a predetermined position relative to the outline of the substrate, the apparatus comprising:
 a sheet of material having:
  a hole therethrough, the hole conforming to the outline of the substrate; and
  an upper surface with markings, the markings defining the predetermined position of the reflective element within the hole.

2. The apparatus according to claim 1, wherein the sheet is thin or substantially rigid.

3. The apparatus according to claim 1, wherein the sheet carries identification markings on its upper surface.

4. The apparatus according to claim 3, wherein the markings include a barcode.

5. The apparatus according to claim 1, wherein the markings include lines.

6. The apparatus according to claim 5, wherein the markings form two or more lines.

7. The apparatus according to claim 6, wherein the lines intersect within the outline of the upper surface of the apparatus.

8. The apparatus according to claim 7, wherein the lines intersect within the hole in the sheet.

9. The apparatus according to claim 1, further comprising an adhesive applied to a surface of the sheet opposite the upper surface.

10. A method of placement on a surface of an optical marker for radiotherapy comprising:
 projecting an image onto the surface to identify a position on the surface where the optical marker is to be placed;
 aligning a sheet with the projected image so that a hole in the sheet is located in a predetermined position or orientation relative to the position; and
 aligning the optical marker with the hole in the sheet.

11. The method according to claim 10, further comprising fixing the optical marker to the surface and then removing the sheet.

12. The method according to claim 10, further comprising:
 prior to aligning the sheet, placing the surface to which the optical marker is to be placed onto a movable support surface;
 placing the optical marker on the surface at the desired placement location and
 moving the support surface relative to the projected image so that the projected image coincides with a reflective portion of the optical marker.

13. The method according to claim 10, wherein the surface to which the optical marker is to be placed is a surface of an apparatus for radiotherapy.

14. The method according to claim 10, wherein the surface to which the optical marker is to be placed is a surface of a patient to be subjected to radiotherapeutic treatment.

* * * * *

UNITED STATES PATENT AND TRADEMARK OFFICE
CERTIFICATE OF CORRECTION

PATENT NO. : 9,486,648 B2  
APPLICATION NO. : 14/466558  
DATED : November 8, 2016  
INVENTOR(S) : Peter Carey et al.

Page 1 of 1

It is certified that error appears in the above-identified patent and that said Letters Patent is hereby corrected as shown below:

On the Title Page
Item (72), in the Inventors, Line 2:
"Paul Barry, Quebec (CA)" should read --Paul Barry, Brandon, FL (US)--.

Signed and Sealed this
Thirty-first Day of January, 2017

Michelle K. Lee
*Director of the United States Patent and Trademark Office*